(12) United States Patent
Klitmose et al.

(10) Patent No.: US 6,796,970 B1
(45) Date of Patent: Sep. 28, 2004

(54) DOSE SETTING DEVICE

(75) Inventors: Lars Peter Klitmose, Gentofte (DK); Henrik Andersen, Vaerloese (DK); Preben Broskov Nielsen, Gilleleje (DK); John Thrane Hansen, Vipperød (DK)

(73) Assignee: Novo Nordisk A/S, Bagsvaerd (DK)

( * ) Notice: Subject to any disclaimer, the term of this patent is extended or adjusted under 35 U.S.C. 154(b) by 0 days.

(21) Appl. No.: 09/090,144

(22) Filed: Jun. 4, 1998

Related U.S. Application Data

(60) Provisional application No. 60/050,993, filed on Jun. 18, 1997.

(30) Foreign Application Priority Data

Jun. 17, 1997 (DK) .............................. 0706/97

(51) Int. Cl.[7] ................................. A61M 5/00
(52) U.S. Cl. ..................... 604/207; 604/148; 604/154; 604/218; 604/200; 604/224; 604/244; 128/DIG. 1; 222/326
(58) Field of Search ............................... 604/131, 134, 604/135, 139, 148, 151, 152, 154, 155, 187, 218, 207–211, 200–202, 224, 228, 232, 236, 244; 128/DIG. 1, DIG. 12; 222/386, 326, 309

(56) References Cited

U.S. PATENT DOCUMENTS

| | | | | |
|---|---|---|---|---|
| 4,298,000 A | * | 11/1981 | Thill et al. ................... | 604/135 |
| 4,313,439 A | * | 2/1982 | Babb et al. .................... | 604/28 |
| 4,493,704 A | * | 1/1985 | Beard et al. .................. | 604/154 |
| 4,676,122 A | * | 6/1987 | Szabo et al. .................. | 604/135 |
| 5,064,098 A | * | 11/1991 | Hutter et al. ................ | 222/137 |
| 5,176,646 A | * | 1/1993 | Kuroda ....................... | 604/154 |
| 5,611,784 A | * | 3/1997 | Barresi et al. .............. | 604/224 |
| 5,637,095 A | * | 6/1997 | Nason et al. ................ | 604/135 |
| 5,957,889 A | * | 9/1999 | Poulsen et al. ............. | 604/131 |

FOREIGN PATENT DOCUMENTS

| | | |
|---|---|---|
| EP | 0 327 910 | 8/1989 |
| WO | WO 87/02895 | 5/1987 |

* cited by examiner

*Primary Examiner*—Loan H. Thanh
*Assistant Examiner*—Cris L. Rodriguez
(74) *Attorney, Agent, or Firm*—Reza Green, Esq.; Richard W. Book, Esq.; Marc A. Began, Esq.

(57) ABSTRACT

A dose setting device for a delivery system has a piston rod (6, 9) which successively presses a piston (2) into a cylinder ampoule (1). Doses are set by rotating a second part (9) of the piston rod (6, 9) in relation to a first part (6). The two parts are connected by mating threads so that the total length of the piston rod (6, 9) is increased proportional to the angle of rotation, and a point (18) on the second part is moved away from a stop position fixed in relation to a housing (5) The set dose is delivered when the point (18) is moved back to the stop position. The first part (6) can be axially displaced but not rotated in the housing (5), and the second part (9) can both rotate and be axially displaced. The first part (6) is maintained in abutment with the piston (2) and the second part (9) is coupled to be rotated by a dose setting wheel (20). An injection push button (10) is movable between a projecting position and a pressed home position and has elements (13) acting on the second part (9) to press this part to its stop position.

10 Claims, 6 Drawing Sheets

DOSE SETTING DEVICE

CROSS-REFERENCE TO RELATED APPLICATIONS

This application claims priority under 35 U.S.C. 119 of Danish application serial no. 0706197 filed Jun. 17, 1997, the contents of which are fully incorporated herein by reference.

The present application claims priority on U.S. provisional application No. 60/050,993, filed on Jun. 18, 1997.

BACKGROUND OF THE INVENTION

The invention relates to a dose setting device for a drug delivery system of the kind wherein a piston rod is successively pressed into a first end of a cylinder ampoule containing a drug to be delivered to press a piston closing said first end of the ampoule into the ampoule so that the drug is pressed out through a delivery member mounted at a second end of the ampoule. Dose setting is provided by rotating a second part of the piston rod in relation to a first part of said piston rod, which parts are connected by mating inner and outer threads on the respective parts, so that the total length of the piston rod is increased by a distance which is proportional with the extent of the rotation of the parts. When so rotated, a point on the second part of the piston rod is moved away from a stop position fixed in relation to a housing so that the set dose is delivered when said point is moved back to the stop position. The first part of the piston rod is guided in the housing so that it can be axially displaced but not rotated, and the second part of the piston rod remote from the piston is mounted so that it can be as well rotated as axially displaced.

EP 327 910 discloses a device by which doses may be set by increasing the total length of a piston rod, which abuts a piston of an ampule in the device, and a piston rod extension which is through a thread connection coupled to the piston rod. The increase is obtained by rotating the piston rod extension relative to the piston rod, by rotating a dose setting member which can be rotated relative to the housing and consequently relative to the piston rod. A connection between the dose setting member and the piston rod extension makes the piston rod extension follow the rotation of the dose setting member. By the resulting increase of the total length of the piston rod and its extension, the outer end of the piston rod extension, which was previously flush with the end of the housing is passed out through the end of the housing. The projecting end of the piston rod extension is used as an injection button which can be pressed until it again is flush wit the housing. The piston is thereby pressed into the ampoule a distance corresponding to the set increase of the total length of the piston rod and the piston rod extension. This setting and injection process can be repeated until the ampoule is empty and the piston rod and its extension have reached a maximal length, at which time the whole device is disposed of.

Similar dose setting devices are used in durable devices wherein only the ampoule is replaced by a new one when empty. Before a new ampoule can be mounted in the device, it is necessary to screw the two parts of the piston rod together to reduce the total length of said piston rod including its extension to the original length it had before the length was increased through repetitive dose settings. As mentioned, the two parts have to be screwed together manually, or the thread may be made with a pitch by which the angle of friction for the piston rod material is exceeded so that the parts, if allowed to, will rotate relative to each other and this way be screwed into each other when the parts are pressed axially towards each other. Also, the threads may be formed so that they may be drawn out of their mutual engagement when they are pressed towards each other. This axial pressing may be resulted by movement of a part of the housing of the device in order to obtain access to the space accommodating the ampoule.

In the device described in EP 327 910, the end of the piston rod projects from the end of the syringe a distance corresponding to the set dose. In the case of small doses, this distance may be very small, less than 1 mm. It may be desirable that the injection button has to be moved the same distance independent of the dose which is going to be injected.

A device wherein that wish is met is described in EP 235 312. In this device, an injection button with a push rod is reciprocated between fixed end positions. The push rod has a length allowing it just to abut the piston in the ampoule when the injection button is pressed home. If the length of the push rod is increased by a distance corresponding to a set dose when the rod is in its retracted position, it will, the next time the button is pressed home, press the piston into the ampoule a distance corresponding to the elongation provided by the setting of the dose. After the injection, the push rod will again be withdrawn from the piston. When the ampoule is empty, the push rod has been elongated to about twice its original length and before a new ampoule can be mounted in the device, the push rod must be screwed back to its original length. A drawback by this device is that the push rod is drawn away from the piston when the injection is finished and the button is no longer pressed. When this occurs, the piston, due to its elasticity and due to the pressure in the ampoule, may move backwards in the ampoule, whereby the just injected dose as well as the subsequent one are made imprecise.

Whereas injection devices so far has been given the shape of a fountain pen, a trend now points towards shorter devices which rather have the shape of a large lighter or a small pack of cigarettes. A reason for this development may be that ampoules with larger content, 3 ml instead of previously 1.5 ml, requires a pen diameter which makes it impossible to maintain the fountain pen illusion.

Whereas the device according to EP 327 910 could be provided with a flexible piston rod to adapt it to a short device, the device according to EP 245 312 is not suited for such adapting as the whole piston rod and its extension have to reciprocate in a guide which guides a flexible rod. Whereas the resistance against the movement of a flexible piston rod through a piston rod guide may serve as a barring against backwards moving of the piston rod, it will be unacceptable if the piston rod shall be reciprocated as reciprocation is conditioned on a reset spring which can overcome said resistance. When an injection is made the injection button must be pressed with a force which overcomes as well the resistance in the guide, the force of the spring; and the force necessary to press a liquid out from the ampoule and inject it.

BRIEF SUMMARY OF THE INVENTION

It is an object of the invention to provide a dose setting device which is suited for short devices.

This is obtained by a device as described in the opening of this application, which device according to the invention is characterised in that the fist part of the piston rod is maintained in abutment with the piston in the cartridge, that the second part of the piston is coupled to a gear engaging a gear on a dose setting wheel to be rotated when said dose setting wheel is rotated, and that an injection mechanism is provided comprising a push button which can be moved between a projecting position and a pressed home position, and which injection mechanism has elements acting on the second part of the piston rod to press this second part to its stop position when the push button is pressed home.

In an embodiment of the device according to the invention the threads may be not self locking, the gear engaging the teeth of the dose setting wheel may be locked against unintentional rotation in relation to the housing, and the stop position may be defined by an end position of a surface of a lifter forming a part of the injection mechanism. The lifter reciprocates between fixed end positions, and said point of the second part of the piston rod may be defined as an endpoint at an end of this second part of the piston rod, which endpoint in abutment with said surface, forms a pivot about which the second part of the piston rod can rotate when not locked against such rotation.

When the threads connecting the two piston rod parts are not self locking, the two parts may be pressed together if they are allowed to rotate in relation to each other. However, the first part cannot rotate relative-to the housing and as the second part carries a gear engaging the teeth of a toothed dose setting wheel, which is again locked against unintentional rotation in relation to the housing, the two parts cannot be rotated relative to each other unless special precautions are taken. A movement of the injection member a constant distance each time an injection button is pressed is ensured by the provision of an injection member which can be reciprocated between fixed end positions. When this member is in its end position defined by the fact that an injection button is pressed home, a surface of the member defines the stop position to which a point of the second part of the piston rod is moved when the injection button is pressed home. The fact that said point is an end point at the outer end of the second part of the piston rod, which endpoint in abutment with said surface forms a pivot about which the second part of the piston rod can rotate when not locked against such rotation, ensures that the piston rod will either transmit axial forces from one end of the piston rod to the other or its parts will rotate so that the two parts are screwed together and the active piston rod is shortened. If the dose setting wheel is voluntarily rotated to set a dose, the two piston rod parts are rotated relative to each other to change the length of the piston rod in accordance with the relative rotation as the rotation of the dose setting wheel is transmitted to the second piston rod part through the gear.

According to an embodiment of a device according to the invention, a connection from a lid covering the ampoule may force the piston rod away from-the piston, unlock the dose setting wheel for rotation, and move the second part of the piston rod towards said surface of the lifter to make said end point of this second part abut said surface when the lid is opened. When the first part of the piston rod is drawn away from the piston, the nut member will be pressed towards said surface of the lifter and due to the threads being not self locking and due to the second part of the piston rod being freely rotatable the nut member will induce a rotation of said second part of the piston rod and this way be moved to the other end of said second part of the piston rod to be ready for a new series of dose settings and injections.

In a preferred embodiment of a device according to the invention, the threads may be self locking, the stop position may be defined by a beam fixed in the housing which beam may be abutted by a member fixed to the second part of the piston rod, and the nut member may be so designed that its thread can be coupled free from its engagement with the thread of the second part of the piston rod.

Self locking threads may have a smaller pitch than threads which are not self locking and a lower pitched thread gives a more precise setting of a dose. With self locking threads rotation of the second part of the piston rod does not occur when the nut element is moved along this part, and the nut element has to be de-coupled from its engagement with the thread on the second part of the piston rod in order to be moved along said second part without this part being rotated. This movement may Appropriately be induce by a connection from the lid covering the ampoule when said lid is opened to replace an empty ampoule.

To obtain said de-coupling, this nut member may have two intersecting bores of which one bore has an inner thread matching the outer thread of the second part of the piston rod and the other bore is smooth and fits slidingly over the thread of the second part of the piston, the nut member being tiltably mounted relative to the first part of the piston rod so that the threaded bore is concentric with the second part of the piston rod during the dose setting and injection and is tilted by said connection which act on the nut member to bring the smooth bore to a position concentric with said second part of the piston during withdrawal of the piston rod.

BRIEF DESCRIPTION OF THE SEVERAL VIEWS OF THE DRAWINGS

In the following the invention will be described in further details with reference to the drawings, wherein.

DETAILED DESCRIPTION OF THE INVENTION

Figure 1:
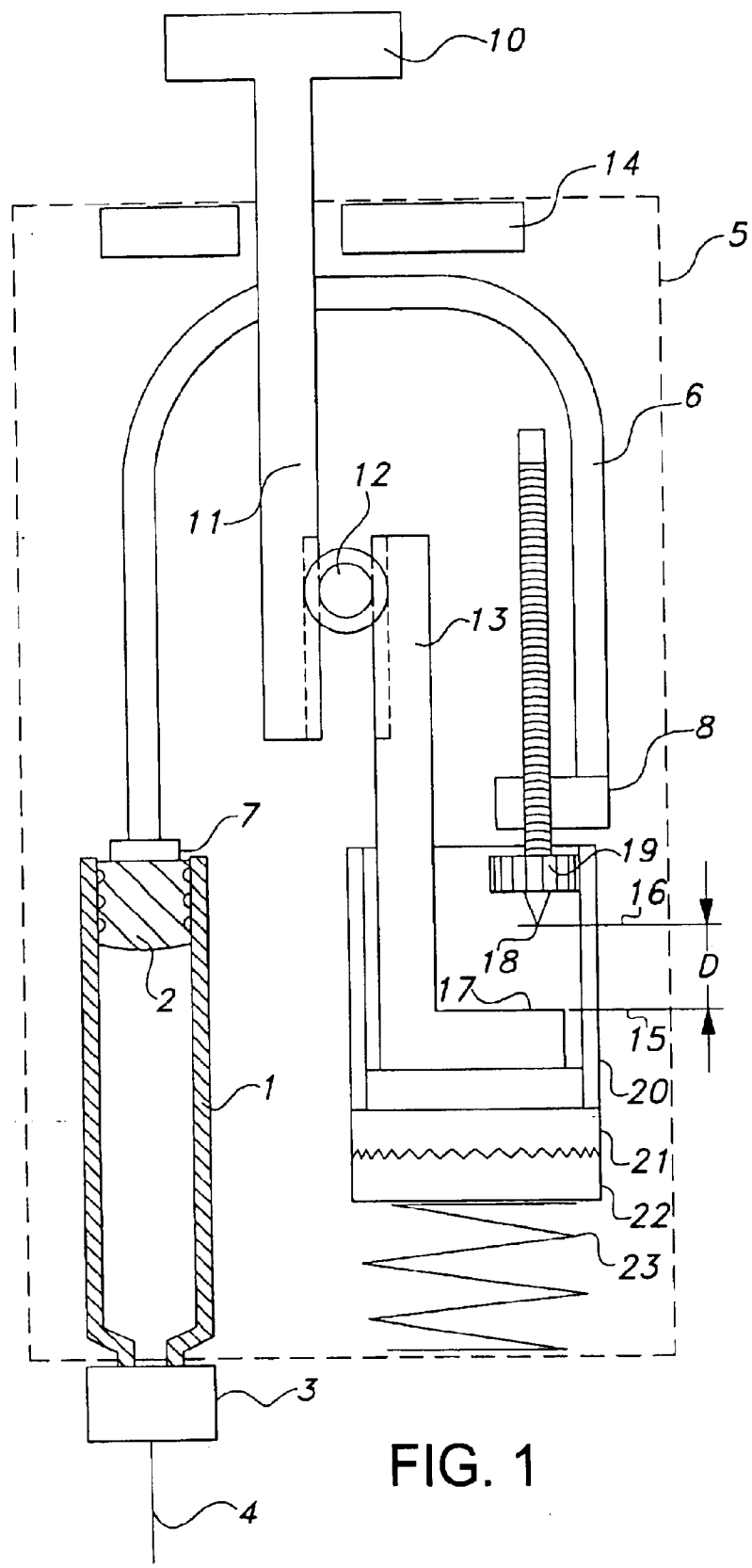
FIG. 1 shows schematically a syringe with a dose setting mechanism according to the invention in a condition ready for dose setting.

In FIG. 1 an ampoule 1, which is at one end closed by a piston 2 and at the other end closed by a rubber membrane (not shown) to receive a needle hub 3 with an injection needle 4, is contained in the housing 5 of an injection device, the housing 5 being indicated by a broken line.

The piston 2 is acted upon by a flexible piston rod comprising a first flexible part 6 which may, e.g., be made as a tightly wound helix of resilient steel. One end of the flexible part 6 acts on the piston 2 through a piston rod shoe 7. The other end, which is deflected 180° from the first end by a guide (not shown), is provided with a nut member 8 having an internally threaded opening. An externally threaded spindle 9 is carried in this opening with its thread engaging the internal thread in the opening of the nut member 8. This spindle forms a second part of the piston rod. By rotation of the spindle 9 in the nut member 8 the total length of the piston rod may be changed by varying the part of the second part of the piston rod which lies in extension of the first part 6.

An injection mechanism comprises an injection button 10 at an end of a cogged bar 11, a gear 12, and a lifter 13 having a cogged arm. The cogs of the bar 11 and the cogs of the arm of the lifter 13 are at diametrically opposed sides engaged by the gear 12, which can rotate about a pin fixed in the housing whereby a downward movement of the button 10 and the bar 11 is converted to an upward movement of the lifter 13 which can press the outer end of the spindle 9 and thereby press the piston rod in an axial direction so that this piston rod forces the piston 2 further into the ampoule 1.

When the device is made ready for injection, a spring (not shown) will force the press button 10 to the projecting position relative to the housing 5 and the lifter 13 to a lowermost position, as shown in FIG. 1. To perform an injection, the button 10 is pressed home to abutment with the housing 10 where abutting parts 14 are indicated. Stops (not shown) define the extreme positions of the parts of the injection mechanism. These extreme positions are indicated by lines 15 and 16 indicating the lowers most position and uppermost position, respectively, of a surface 17 on the lifter 13. The distance between the lines 15 and 16 is marked as D.

In FIG. 1 the outer end point 18 of the spindle 9 lies at the line 16. It was pressed to this position by the lifter 13 the last time the button 10 was pressed home to abutment with the housing. A dose may now be set by screwing the spindle 9 outwardly in the nut member 8 to make its end point 18 lie between the lines 15 and 16. The size of the dose is defined by the distance between the end point 18 and the line 16 as the endpoint 18 will be moved back to this line when the button 10 is pressed home.

The spindle 9 is provided with a gear 19 engaging inner teeth on a dose setting drum 20. The drum has a bottom 21 with radial knurls engaging corresponding radial knurls on a disc 22 which is by a spring 23 pressed against the bottom 21 of the drum 20, the knurls being so designed that they with hearable clicks tide over each other each time the drum 20 is rotated a certain angle, e.g., corresponding to an altering of the dose setting by one unit. A dose can be set by rotating the drum 20. This rotation will be transmitted to the 9 spindle which is screwed outwardly in the nut member 8 a distance corresponding to the rotation of the dose setting drum 20. It should be noted that, if too large a dose is set, it may be reduced by rotating the drum 20 in the opposite direction.

The rotation of the dose setting drum 20 is sensed electronically and is transmitted to a display whereby the size of the figures on the display is independent of the physical size of the dose setting drum 20 and all other advantages obtained by using electronic settings and displays are obtained.

Figure 2:
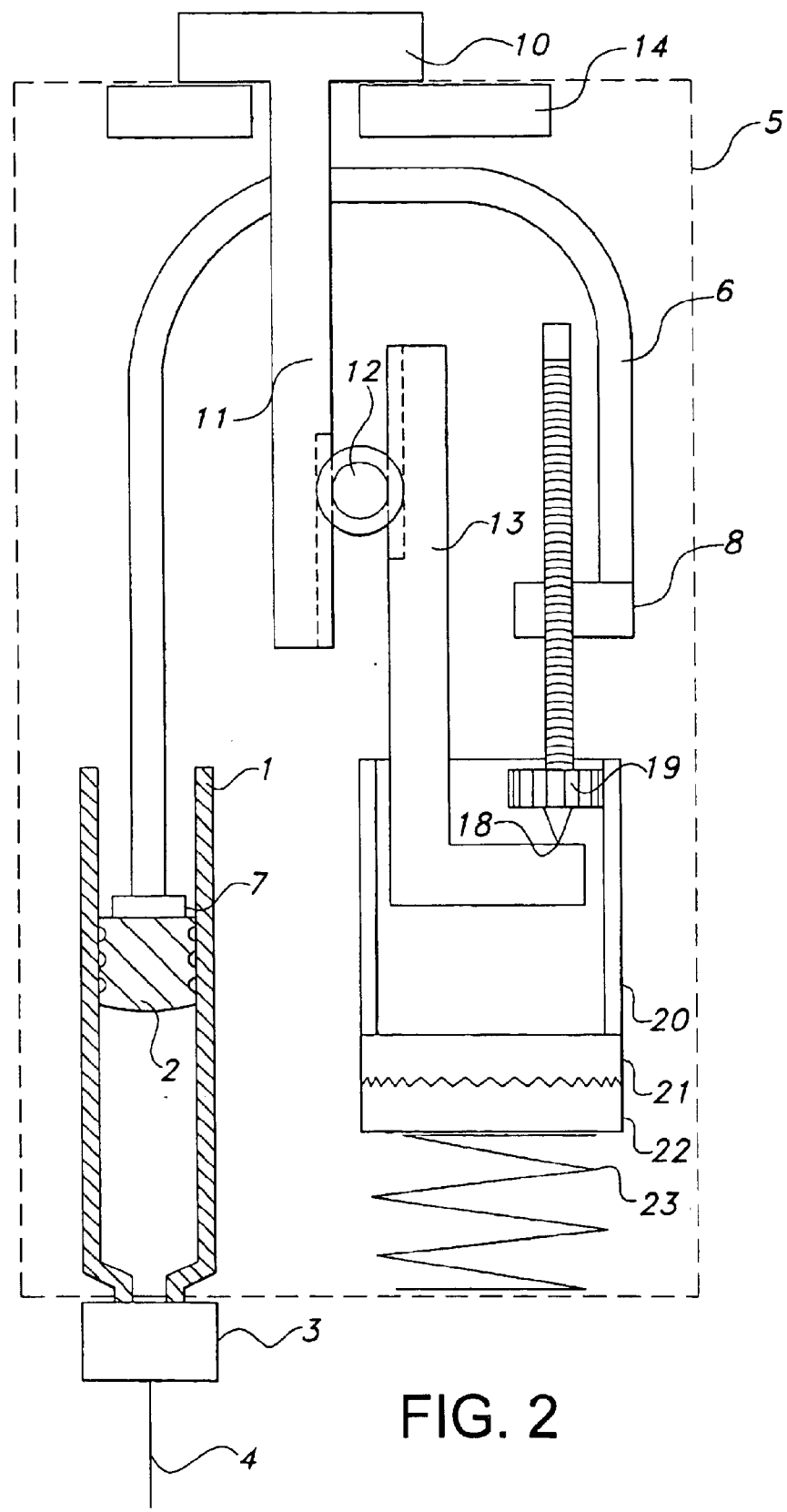
FIG. 2 shows there in FIG. 1 in a condition at the end of an injection.

FIG. 2 shows the device with the press button 10 pressed home to abutment with the housing as it appears after a dose has been injected. A lock (not shown) is provided keeping the button 10 in this position until it is released again, e.g., when the dose setting drum 20 is operated. Also, when the apparatus is stored away until the next injection, the press button 10 is maintained in this pressed home position.

Figure 3:
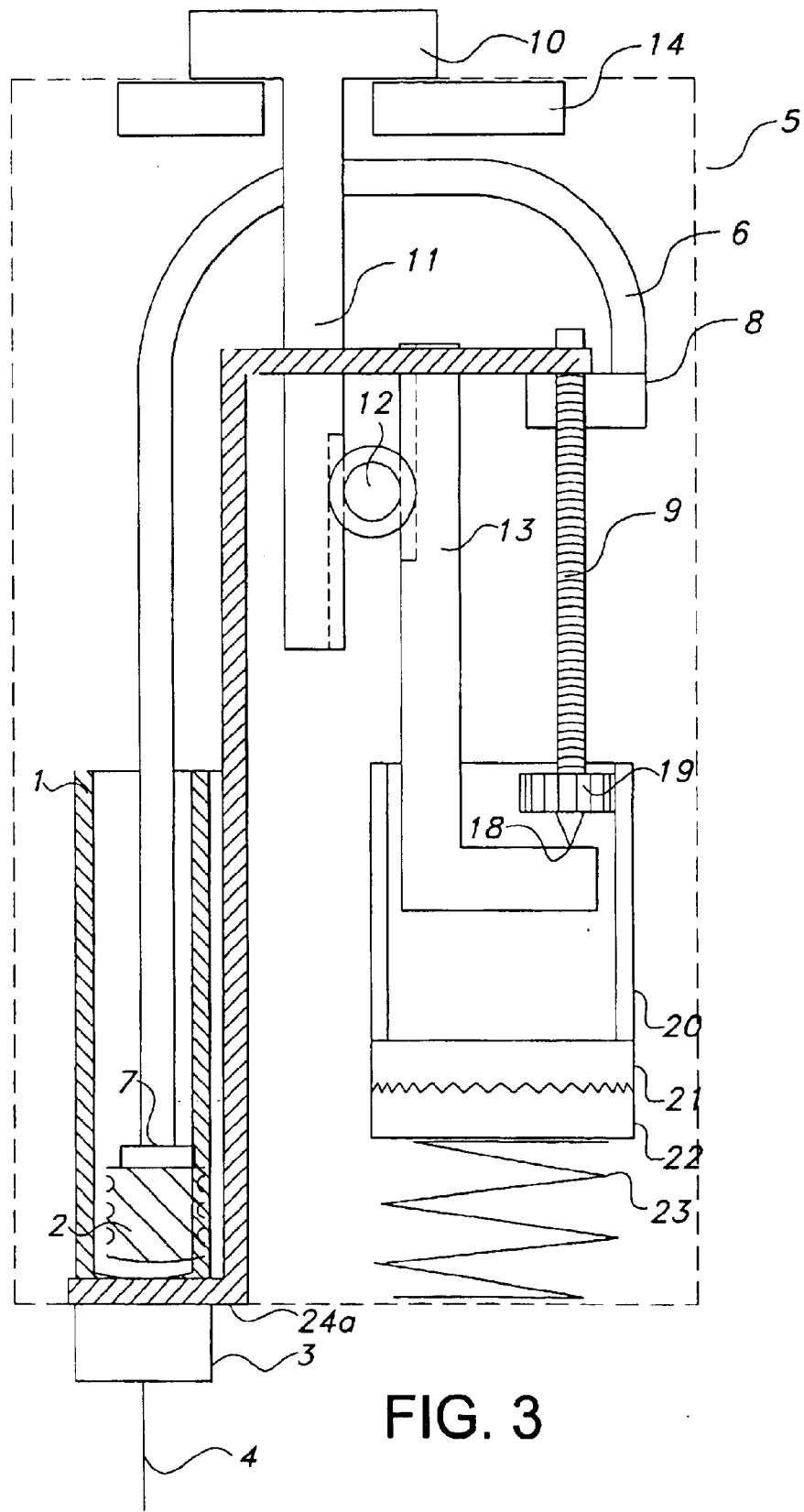
FIG. 3 shows the syringe in FIG. 1 in a condition where the ampoule is just empty.
Figure 4:
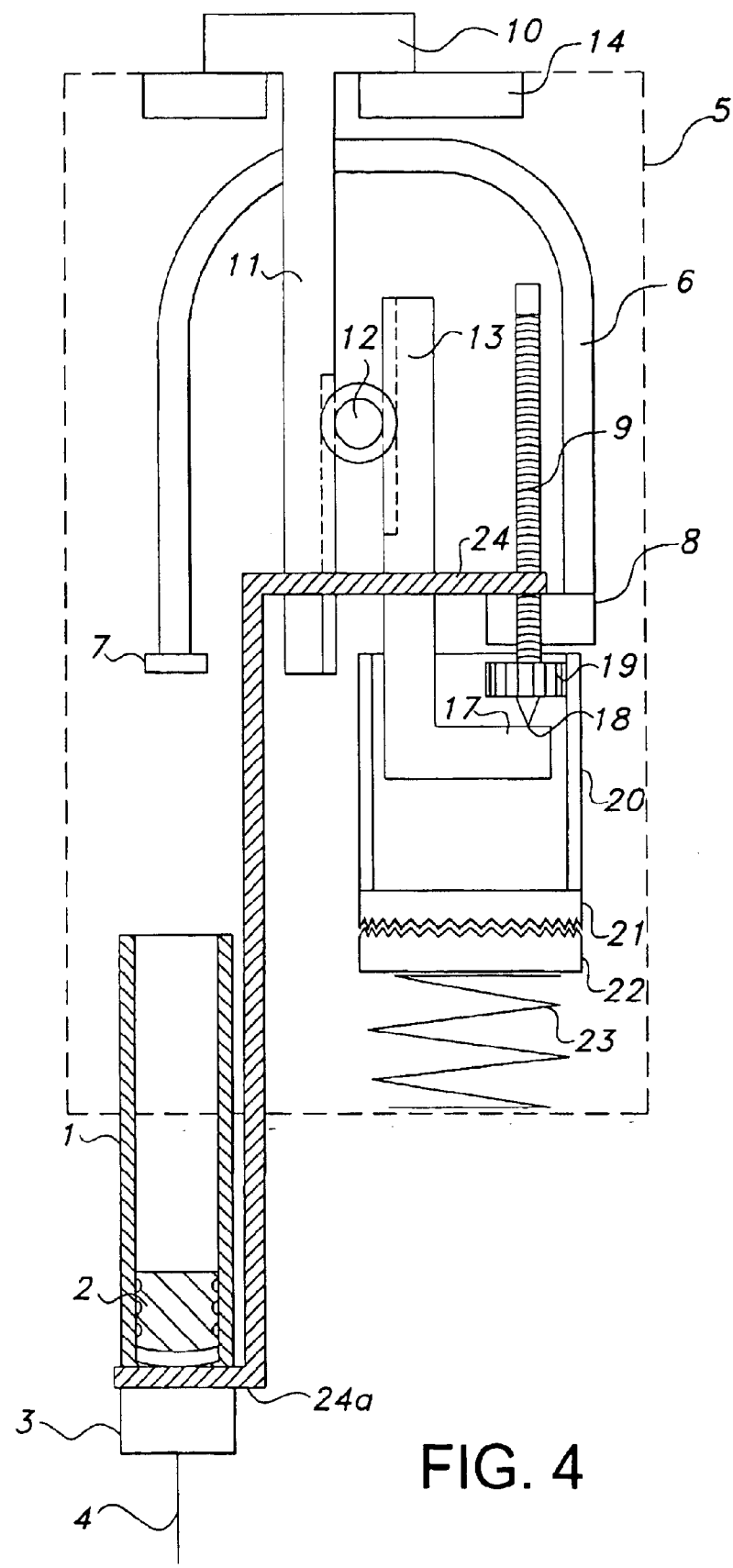
FIG. 4 shows the syringe in FIG. 1 in a condition wherein it opened for replacement of an empty ampoule.

FIG. 3 shows the device in the same condition as FIG. 2 but in FIG. 3 the ampoule 1 is empty. The device shown in FIG. 3 also includes a piston rod withdrawal element 24 which is connected to a drawer element 24a in which the ampoule is held. FIG. 4 shows how the element 24 moves the nut member 8 towards the surface 17 of the lifter 13 when the ampoule 1 is drawn out to be changed. As the button 10 is locked in the pressed home position, the end tip 18 of the spindle abuts the surface 17 of the lifter which is consequently locked in its shown position. The surface 17 and the tip 18 form a pivot about which the spindle can rotate if allowed to. When the ampoule drawer 24a is opened, the disc 22 is initially drawn away from the bottom 21 of the dose setting drum 20 and this way the dose setting drum 20 is set free to rotate. A condition which must be fulfilled in this embodiment is that the engaging threads of the spindle 9 and the nut member 8 are not self locking, i.e., that the angle of inclination of the thread is larger than the angle of friction for the threaded materials.

Figure 5:
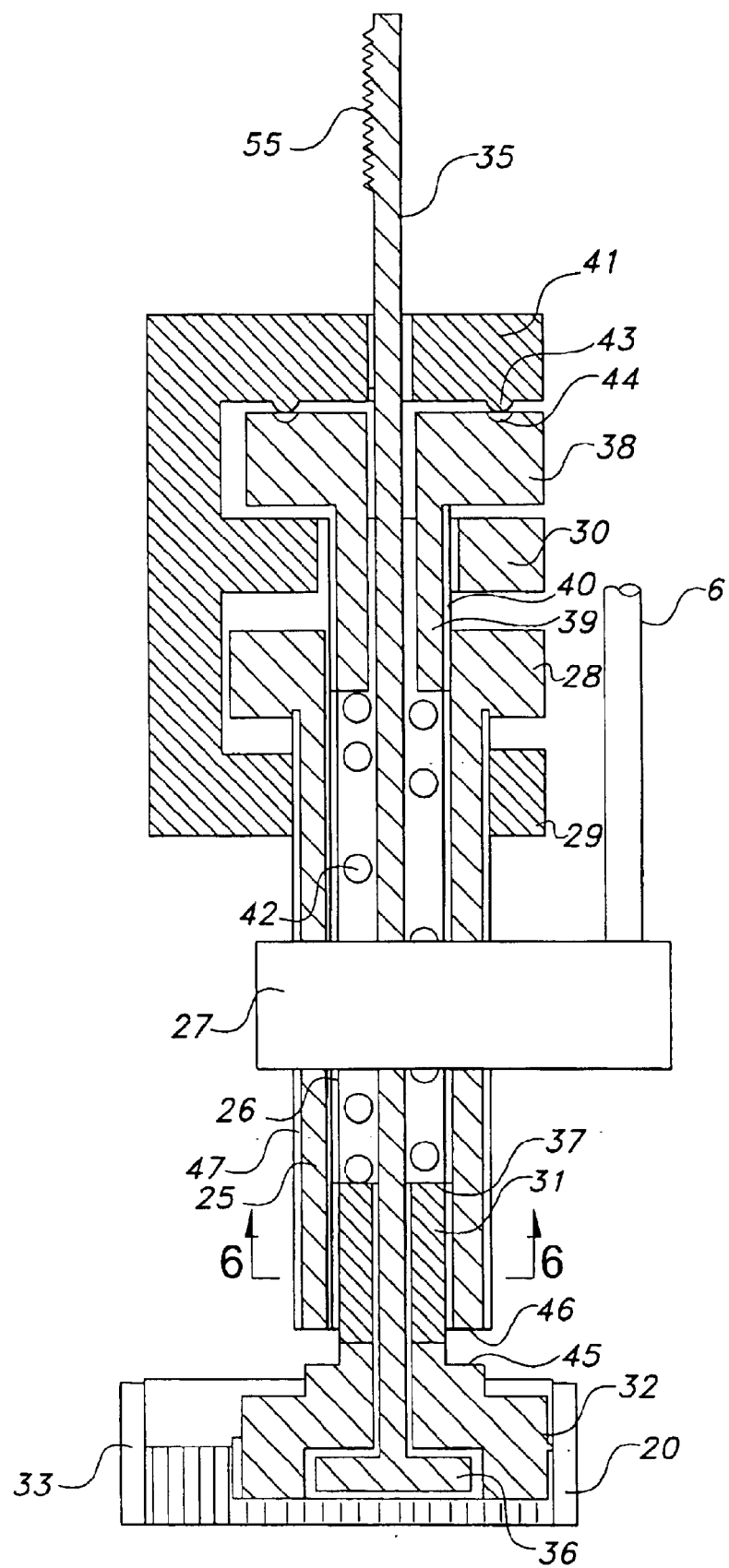
FIG. 5 shows schematically a detail of another embodiment of the dose setting mechanism.

FIG. 5 shows a detail of another embodiment of a dose setting mechanism according to the invention. In this embodiment, a spindle 25 forming the second part of the piston rod has an axial bore the inner wall of which is provided with a number of longitudinal grooves 26. The spindle 25 is screwed through a nut member 27 at the end of the flexible first part 6 of the piston rod whereby the spindle 25 is divided into a projecting part forming an extension of the first part 6 of the piston rod and a part lying behind the nut member 27. Said part lying behind the nut member 27 is guided rotatable and axially so as to be displaceable in an opening in a lower beam 29 of Reshaped construction fixed in the housing. A flange 28 at the end of the spindle 25 limits the axial movement of said spindle and in this way also its rotatability as the spindle 25 will through its engagement with the nut member 27 be longitudinally displaced when rotated until the flange 28 abuts either a middle beam 30 of the E-shaped construction or the lower beam 29 of this construction. The beams 29, 30 act as stops limiting the axial movement of the spindle 25.

Figure 6:
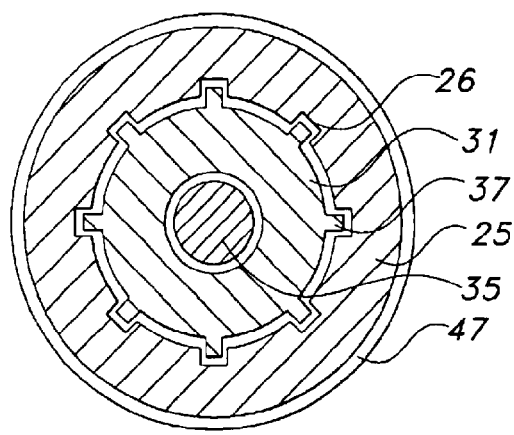
FIG. 6 shows a sectional view along the line VI–VI in FIG. 5.

A mainly cylindrical carrier 31 is inserted in the projecting end of said spindle 25. The carrier 31 has on its outer cylindrical wall longitudinal splines 37 engaging the longitudinal grooves 26 in the inner wall of the bore in the spindle 25, as it is seen in FIG. 6, so that rotation of the carrier 31 is transmitted to the spindle 25, whereas the carrier 31 can be moved axially along the spindle 25. At its outer end surface the carrier 31 is knurled to engage corresponding knurls on a gear element 32, which has teeth engaging an inner toothed rim 33 in a dose setting drum 34.

A pin 35 running all the way through axial bores in the gear element 32 and the carrier 31 is, at its end projecting through the gear element 32, terminated by a disc 36 secured to said pin 35. The pin 35 extends through the bore of the spindle 25 and through a bore in a counting element 38 mounted on a mainly cylindrical stem 39 inserted in the end of the spindle 25 which caries the flange 28. The outer cylindrical wall of the stem 39 is provided with splines 40 engaging the grooves 26 in the spindle 25 so that said stem can be displaced axially but must follow the rotation of the spindle 25. The counting element 38 is placed between the middle beam 30 and an upper beam 41 of the E-shaped construction and has at its outer wall not shown means for activating not shown contacts or sensors fixed in the housing to monitor the extent of rotation of the counting member 38 and consequently of the spindle 25 which said counting member is bound to follow.

The pin 35 extends through the stem 39, the counting element 38, and the upper beam 41 of the E-shaped construction and is at its upper end provided with a toothing 55 engaging a gear corresponding to the gear 12 in FIGS. 1–4 so that the pin 35 carries out the function of a lifter.

The elements inserted in the respective ends of the spindle 25, i.e., the carrier 31 and the stem 39, are pressed away from each other by a spring 42 positioned in the bore of the spindle 25. Thereby the knurls of the carrier 31 are pressed into engagement with the knurls of the gear element 32 and an end wall of the counting element 38 is pressed into abutment with a surface of the upper beam 41 of the E-shaped construction. Said surface of the upper beam 41 is provided with protrusions 43 which engage mating depressions 44 in the end wall of the counting element.

When a dose is set by rotating the dose setting drum 34, the toothed rim 33 of this drum will rotationally drive the gear element 32 from which rotation will be transmitted via the cattier 31 to the spindle 25 unless the spindle is in a position wherein its flange 28 abuts the lower or middle beams 29 or 30 respectively, and the rotation is in a direction which further moves the flange towards the beam in question, in which case the coupling formed by the knurled surfaces of the gear element 32 and the carrier will be released by the knurls sliding over each other as the carrier 31 may be pressed away from the gear element against the force of the spring 42. This way transmission of rotational forces which could be damaging to the device is avoided. By an injection the flange 28 will be moved to abut the middle beam 30 of the E-shaped construction.

From this position a dose is set by screwing the flange 28 away from the intermediate beam 30. The size of a set dose is determined by the distance established between the flange 28 and the middle beam 30 and a limit to the dose which can be set is determined by the rotation needed to make the flange abut the lower beam 29 of said E-shaped construction.

When the spindle 25 is rotated the stem 39 with the counting element 38 will follow this rotation and the protrusions 43 on the upper beam 41 will slide out of the depressions 44 pressing the counting element 38 away against the force of the spring 42 until the projections meet new depressions to engage. The protrusions and depressions may be provided with a circumferential spacing which makes the number of clicks provided by the successive engagements indicate the size of a dose set.

When a dose is set, and the flange 28 thereby is moved away from the intermediate beam 30 of the E-shaped construction, injection may be performed by pressing the injection button of the device to draw the lifter (i.e., pin 35) towards the end of the piston rod. The spindle 25 forming the second part of the piston rod is acted upon by a shoulder 45 on the gear element abutting an end surface 46 of the spindle 25, and pulled upwardly until the flange 28 again abuts the intermediate beam 30.

A play between the shoulder 45 and the end surface 46 ensures that the gear element 32 is drawn out of engagement with the toothed rim 33 before or at an early stage of the injection. This way the dose setting drum is set free so that the size of the dose cannot be influenced during the injection. It must be noticed that the injection button must have a stroke sufficient to allow the lifter to lift the gear element 32 free of the toothed rim 33 and to move the spindle a distance corresponding to the maximal dose which can be set.

The engaging threads of the nut member 27 and the spindle 25 are self locking. This allows a smaller pitch of the threads and ensures, a more precise dosing. However, precautions must be taken to ensure that the thread of the nut member 27 can be drawn out of engagement with the thread of said spindle 25 so that the nut member 27 can be moved from one end of this spindle to the other without rotating the spindle when the piston rod is drawn back to make room for a new filled ampoule when an empty ampoule is drawn out to be replaced.

Figure 7:
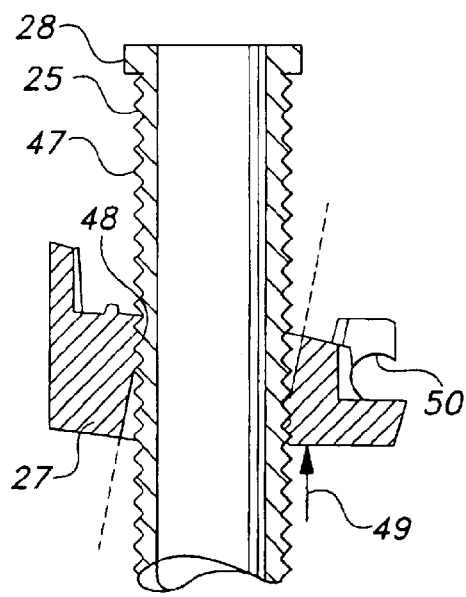
FIG. 7 shows a sectional view of a tiltable nut member with two bores in a position wherein the threaded bore is concentric with a threaded spindle.
Figure 8:
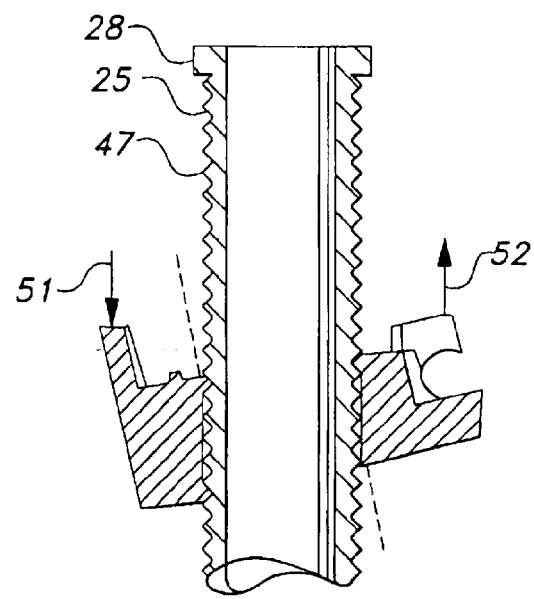
FIG. 8 shows the nut member in FIG. 7 tilted to a position wherein its smooth bore is concentric with the spindle.

FIGS. 7 and 8 show a nut member 27 having a first and a second bore, the axes of which are intersecting by making an acute angle with each other. The first bore has a diameter corresponding to the outer diameter of the threaded piston rod 25 and the second bore having an inner thread mating with the outer thread 47 of said piston rod only on parts of this second bore which are not comprised by the first bore.

During dose setting and injection, the nut member 27 is in the position shown in FIG. 7 with its second bore coaxial with the spindle 25 and the thread 48 in this bore engaging the thread 47 of said spindle 25. When the spindle is screwed downward in the nut member 27 to set a dose or is lifted upward to inject a set dose it will try to rotate the nut member in the direction of the arrow 49 about a not shown pivot pin at the end of the first part of the piston rod which pivot engages a journal 50 arranged on the nut member 27. When the nut member by a piston rod withdrawal element is acted upon at an edge diametrically opposite the pivot pin as indicated by the arrow 51 the nut member 27 is tilted about the pivot pin to bring the first bore to a position wherein it is coaxial with the spindle 25. As the piston rod due to its resistance against withdrawal act on the nut member 27 in the direction of the arrow 52 the nut member 27 will be held in its tilted position wherein it can slide over the top of the thread 47 on the spindle 25 during the withdrawal of the piston rod. In FIGS. 7 and 8 the broken lines indicate the direction of the bore not coaxial with the spindle.

What is claimed is:

1. A drug delivery system comprising:

a housing;

an ampoule accommodated in the housing and having an interior with first and second ends, a piston closing the first end, which piston can be pressed into the ampoule, a membrane closing the second end, and a medicine disposed in the ampoule interior between the piston and the membrane;

a piston rod mounted in the housing and comprising first and second parts, wherein the first part is flexible and has a first end which is maintained in contact with the piston and a second end which is deflected 180 degrees relative to the first end and includes a thread, wherein the second part includes a thread which mates with the thread on the first part so that rotation of the second part relative to the first part changes the total length of the piston rod, wherein the housing includes a guide allowing the first part to move axially but not rotationally, wherein the second part is mounted in the housing for both axial and rotational movement, wherein rotation of the second part relative to the first part causes the second part to move in a first direction away from an initial position to set the amount of a dose, and wherein the second part can be moved in said first direction away from said initial position no more than a maximum distance representing a maximum dose; and an injection mechanism comprising a push button which can be moved between a projecting position and a pressed home position, wherein the injection mechanism includes a piston rod moving element that, responsive to moving the push button from its projecting position to its pressed home position, moves in a direction opposite to said first direction from a first end position to a second end position and engages the second part during at least part of such movement to move the second part back to said initial position upon reaching said second end position, and wherein the distance between the first and second end positions is at least as great as said maximum distance, whereby the distance of movement of the push button is independent of the size of the set dose.

2. A drug delivery system according to claim 1, further comprising a dose setting drum having teeth and supported by the housing, wherein the second part of the piston rod includes a gear engaging the teeth on the dose setting drum, and a mechanism for selectively locking the dose setting drum against unintentional rotation relative to the housing.

3. A drug delivery system according to claim 1, wherein the piston rod moving element comprises a lifter, and wherein the second part of the piston rod has an end point which abuts said lifter when the lifter is in its second end position and during at least part of its movement from the first end position to the second end position.

4. A drug delivery system according to claim 3, wherein the lifter and push button are coupled by gearing to move in opposite directions relative to one another.

5. A drug delivery device according to claim 3, wherein the threads on the first and second parts of the piston rod are not self-locking, and further comprising a drawer element for holding the ampoule and which is moveable between open and closed positions, a piston rod withdrawal element coupled between the drawer element and the piston rod such that, when the drawer element is opened, the piston rod withdrawal element moves the first part of the piston rod towards the lifter, and wherein the end point of the second part abuts the lifter and forms a pivot about which the second part can rotate to allow the second end of the first part to move towards the lifter.

6. A drug delivery system according to claim 5, further comprising a dose setting drum having teeth and supported by the housing, wherein the second part of the piston rod includes a gear engaging the teeth on the dose setting drum, and a mechanism for selectively locking the dose setting drum against unintentional rotation relative to the housing.

7. A drug delivery device according to claim 6, wherein the piston rod withdrawal element is coupled to the piston rod such that, when the drawer is opened, the piston rod withdrawal element unlocks the dose setting drum for rotation.

8. A drug delivery device according to claim 1, wherein the thread on the second part of the piston rod is in the form of a threaded spindle, wherein the thread on the first part is a nut member at the second end of the first part, wherein the nut member is moveable between first and second positions for engaging the spindle and disengaging from the spindle, respectively, wherein the threads on the first and second part of the piston rod are self locking when the nut is in its first position, and further comprising a drawer element for holding the ampoule and moveable between open and closed positions, and a piston rod withdrawal element coupled between the drawer element and the piston rod such that, when the drawer element is opened, the nut is moved to its second position and the second end of the first part of the piston rod is pushed towards the lifter without rotating the spindle.

9. A drug delivery device according to claim 8, wherein the nut member has two overlapping bores at an angle to one another, wherein one bore has an inner thread matching the thread of the spindle and the other bore is smooth and fits slidingly over the spindle, wherein the nut member is tiltably mounted relative to the first part of the piston rod so that the threaded bore is concentric with the second part of the piston rod when in its first position, during dose setting and injection, and is tilted to its second position to bring the smooth bore to a position concentric with the second part of the piston when the drawer is opened.

10. A drug delivery system according to claim 9, wherein the nut member is tilted to its smooth bore position when the nut member is acted on by the piston rod withdrawal element.

* * * * *